United States Patent
LaRose et al.

(10) Patent No.: US 8,852,072 B2
(45) Date of Patent: Oct. 7, 2014

(54) VENTRICULAR ASSIST DEVICE FOR INTRAVENTRICULAR PLACEMENT

(75) Inventors: Jeffrey A. LaRose, Parkland, FL (US); Charles R. Shambaugh, Jr., Coral Gables, FL (US); Steve A. White, Wellington, FL (US); Daniel Tamez, Pearland, TX (US)

(73) Assignee: HeartWare, Inc., Miami Lakes, FL (US)

( * ) Notice: Subject to any disclaimer, the term of this patent is extended or adjusted under 35 U.S.C. 154(b) by 815 days.

(21) Appl. No.: 12/322,746

(22) Filed: Feb. 6, 2009

(65) Prior Publication Data

US 2009/0203957 A1 Aug. 13, 2009

Related U.S. Application Data

(60) Provisional application No. 61/198,682, filed on Nov. 7, 2008, provisional application No. 61/065,140, filed on Feb. 8, 2008.

(51) Int. Cl.
*A61N 1/362* (2006.01)
*A61M 1/12* (2006.01)
*A61M 1/10* (2006.01)

(52) U.S. Cl.
CPC ............... *A61M 1/101* (2013.01); *A61M 1/125* (2014.02); *A61M 1/1008* (2014.02); *A61M 1/122* (2014.02)
USPC .................. 600/16; 600/17; 600/18; 623/3.1; 623/3.13; 623/3.14; 623/3.15; 623/3.23; 623/3.24; 623/3.25

(58) Field of Classification Search
USPC .................... 600/16–18; 623/3.1, 3.13–3.15, 623/3.24–3.26
See application file for complete search history.

(56) References Cited

U.S. PATENT DOCUMENTS

| | | |
|---|---|---|
| 2,941,477 A | 6/1960 | Dalton |
| 3,426,721 A | 2/1969 | Justinien |
| 3,608,088 A | 9/1971 | Dorman |

(Continued)

FOREIGN PATENT DOCUMENTS

| | | |
|---|---|---|
| GB | 1067054 | 4/1967 |
| WO | 9836792 A1 | 8/1998 |
| WO | WO 2006/067473 | 6/2006 |
| WO | WO 2008/106103 | 9/2008 |

OTHER PUBLICATIONS

International Search Report issued by the International Searching Authority (ISA/US) in connection with International Application No. PCT/US09/000762.
Written Opinion of the International Searching Authority issued by the International Searching Authority (ISA/US) in connection with International Application No. PCT/US09/000762.

(Continued)

*Primary Examiner* — Michael Kahelin
*Assistant Examiner* — Mallika D Fairchild
(74) *Attorney, Agent, or Firm* — Lerner, David, Littenberg, Krumholz & Mentlik, LLP

(57) ABSTRACT

A ventricular assist device includes a pump such as an axial flow pump, an outflow cannula connected to the outlet of the pump, and an anchor element. The anchor element is physically connected to the pump, as by an elongate element. The pump is implanted within the left ventricle with the outflow cannula projecting through the aortic valve but desirably terminating short of the aortic arch. The anchor element is fixed to the wall of the heart near the apex of the heart so that the anchor element holds the pump and outflow cannula in position.

20 Claims, 16 Drawing Sheets

(56) References Cited

U.S. PATENT DOCUMENTS

| | | | |
|---|---|---|---|
| 3,685,059 A | 8/1972 | Bokros et al. | |
| 4,437,815 A | 3/1984 | McMullen | |
| 4,589,822 A | 5/1986 | Clausen et al. | |
| 4,595,390 A | 6/1986 | Hakim et al. | |
| 4,615,691 A | 10/1986 | Hakim et al. | |
| 4,625,712 A | 12/1986 | Wampler | |
| 4,642,036 A | 2/1987 | Young | |
| 4,817,586 A | 4/1989 | Wampler et al. | |
| 4,846,152 A | 7/1989 | Wampler et al. | |
| 4,906,229 A | 3/1990 | Wampler et al. | |
| 4,908,012 A | 3/1990 | Moise et al. | |
| 4,927,407 A | 5/1990 | Dorman | |
| 4,994,078 A | 2/1991 | Jarvik | |
| 5,061,256 A | 10/1991 | Wampler et al. | |
| 5,092,879 A | 3/1992 | Jarvik | |
| 5,190,528 A * | 3/1993 | Fonger et al. | 604/171 |
| 5,211,546 A | 5/1993 | Isaacson et al. | |
| 5,290,236 A | 3/1994 | Mathewson | |
| 5,385,581 A | 1/1995 | Bramm et al. | |
| 5,507,629 A | 4/1996 | Jarvik | |
| 5,527,159 A | 6/1996 | Bozeman, Jr. et al. | |
| 5,588,812 A | 12/1996 | Taylor et al. | |
| 5,613,935 A | 3/1997 | Jarvik | |
| 5,713,727 A | 2/1998 | Veronesi et al. | |
| 5,776,190 A | 7/1998 | Jarvik | |
| 5,824,070 A | 10/1998 | Jarvik | |
| 5,840,070 A | 11/1998 | Wampler | |
| 5,888,241 A | 3/1999 | Jarvik | |
| 5,911,685 A | 6/1999 | Siess et al. | |
| 5,924,848 A | 7/1999 | Izraelev | |
| 5,947,892 A | 9/1999 | Benkowski et al. | |
| 6,015,272 A | 1/2000 | Antaki et al. | |
| 6,058,583 A | 5/2000 | Seiss | |
| 6,100,618 A | 8/2000 | Schoeb et al. | |
| 6,120,537 A | 9/2000 | Wampler | |
| 6,135,729 A | 10/2000 | Aber | |
| 6,155,969 A | 12/2000 | Schima et al. | |
| 6,176,822 B1 | 1/2001 | Seiss et al. | |
| 6,227,797 B1 | 5/2001 | Watterson et al. | |
| 6,227,820 B1 | 5/2001 | Jarvik | |
| 6,234,635 B1 | 5/2001 | Seitziner et al. | |
| 6,234,772 B1 | 5/2001 | Wampler | |
| 6,234,998 B1 | 5/2001 | Aber | |
| 6,244,835 B1 | 6/2001 | Antaki et al. | |
| 6,245,007 B1 | 6/2001 | Bedingham et al. | |
| 6,250,880 B1 | 6/2001 | Woodard et al. | |
| 6,254,359 B1 | 7/2001 | Aber | |
| 6,368,083 B1 | 4/2002 | Wampler | |
| 6,439,845 B1 | 8/2002 | Veres | |
| 6,447,265 B1 | 9/2002 | Antaki et al. | |
| 6,447,266 B2 | 9/2002 | Antaki et al. | |
| 6,527,521 B2 | 3/2003 | Noda | |
| 6,595,743 B1 | 7/2003 | Kazatchkov et al. | |
| 6,641,378 B2 | 11/2003 | Davis et al. | |
| 6,688,861 B2 | 2/2004 | Wampler | |
| 6,716,157 B2 | 4/2004 | Goldowsky et al. | |
| 6,717,311 B2 | 4/2004 | Locke | |
| 6,719,791 B1 | 4/2004 | Nusser et al. | |
| 6,752,602 B2 | 6/2004 | Eistrup et al. | |
| 6,869,567 B2 | 3/2005 | Kretchmer | |
| 7,667,218 B2 | 2/2010 | Yamamoto et al. | |
| 1000/0050714 | 10/1875 | Jacob | |
| 2003/0181928 A1 | 9/2003 | Vidlund et al. | |
| 2005/0250975 A1* | 11/2005 | Carrier et al. | 600/16 |
| 2006/0122456 A1 | 6/2006 | LaRose et al. | |
| 2006/0161040 A1* | 7/2006 | McCarthy et al. | 600/16 |
| 2006/0245959 A1 | 11/2006 | LaRose et al. | |
| 2007/0078293 A1 | 4/2007 | Shambaugh, Jr. et al. | |
| 2007/0100196 A1 | 5/2007 | LaRose et al. | |
| 2007/0270839 A1 | 11/2007 | Jeon et al. | |
| 2009/0112312 A1 | 4/2009 | LaRose et al. | |
| 2010/0022939 A1 | 1/2010 | Schima et al. | |

OTHER PUBLICATIONS

Siegenthaler et al. "Mechanical Circulatory Assistance for Acute and Chronic Heart Failure: a Review of Current Technology & Clinical Practice", Journal of Interventional Cardiology, vol. 16/No. 6 (2003) pp. 563-572.

Olsen, Don B. "Presidential Address—The History of Continuous-Flow Blood Pumps", Artificial Organs 24(6), pp. 401-404, Jun. 2000.

Humphrey, Bruce "Coatings—Using Parylene for Medical Substrate Coating", www.devicelink.com/ (Jan. 1996) 5 pages.

MMPA Standard No. 0100-00; Standard Specifications for Permanent Magnet Materials, Magnet Material Producers Association, 1964.

International Search Report issued by the International Searching Authority (ISA/US) in connection with International Application No. PCT/US2005/42495, Apr. 17, 2008.

Written Opinion of the International Searching Authority issued by the International Searching Authority (ISA/US) in connection with International Application No. PCT/US2005/42495, Apr. 17, 2008.

International Preliminary Report on Patentability issued by the International Bureau of WIPO on Mar. 3, 2009 in connection with International Application No. PCT/US2005/42495.

International Search Report issued by the International Searching Authority (ISA/US) in connection with International Application No. PCT/US2005/35964, Oct. 30, 2007.

Written Opinion of the International Searching Authority issued by the International Searching Authority (ISA/US) in connection with International Application No. PCT/US2005/35964, May 31, 2007.

International Search Report issued by the International Searching Authority (ISA/US) in connection with International Application No. PCT/US2006/21544, Dec. 31, 2006.

Written Opinion of the International Searching Authority issued by the International Searching Authority (ISA/US) in connection with International Application No. PCT/US2006/21544, Nov. 29, 2006.

International Preliminary Report on Patentability issued by the International Bureau of WIPO on Apr. 8, 2008 in connection with International Application No. PCT/US2006/21544, Apr. 8, 2008.

Office Action issued Mar. 17, 2008 in connection with U.S. Appl. No. 11/003,810, filed Dec. 3, 2004.

Final Office Action issued Dec. 10, 2008 in connection with U.S. Appl. No. 11/003,810, filed Dec. 3, 2004.

Advisory Action issued Apr. 27, 2009 in connection with U.S. Appl. No. 11/003,810, filed Dec. 3, 2004.

Notice of Allowance issued Aug. 28, 2009 in connection with U.S. Appl. No. 11/003,810, filed Dec. 3, 2004.

Office Action issued Mar. 20, 2008 in connection with U.S. Appl. No. 11/118,551, filed Apr. 29, 2005.

Final Office Action issued Oct. 23, 2008 in connection with U.S. Appl. No. 11/118,551, filed Apr. 29, 2005.

Office Action issued Apr. 17, 2009 in connection with U.S. Appl. No. 11/118,551, filed Apr. 29, 2005.

Office Action issued Sep. 10, 2007 in connection with U.S. Appl. No. 11/243,722, filed Oct. 5, 2005.

Final Office Action issued Jun. 20, 2008 in connection with U.S. Appl. No. 11/243,722, filed Oct. 5, 2005.

Advisory Action issued Oct. 14, 2008 in connection with U.S. Appl. No. 11/243,722, filed Oct. 5, 2005.

Office Action issued Dec. 19, 2008 in connection with U.S. Appl. No. 11/243,722, filed Oct. 5, 2005.

Final Office Action issued Sep. 30, 2009 in connection with U.S. Appl. No. 11/243,722, filed Oct. 5, 2005.

Office Action issued Sep. 22, 2009 in connection with U.S. Appl. No. 11/445,963, filed Jun. 2, 2006.

U.S. Appl. No. 61/135,004, filed Jul. 16, 2008.

International Search Report issued by the International Searching Authority (ISA/US) in connection with International Application No. PCT/US09/000762, Date: Mar. 25, 2009.

Written Opinion of the International Searching Authority issued by the International Searching Authority (ISA/US) in connection with International Application No. PCT/US09/000762, Date: Mar. 11, 2009.

* cited by examiner

FIG. 7
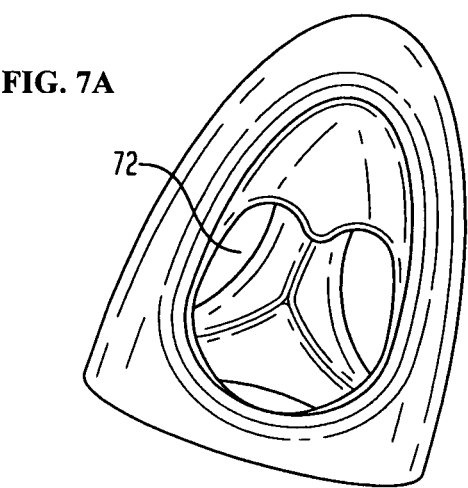
FIG. 7A
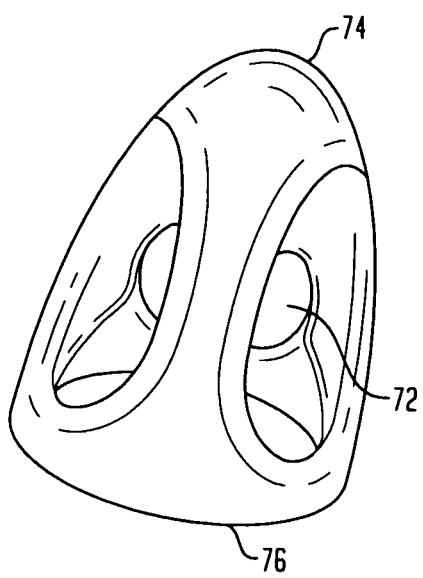
FIG. 7B
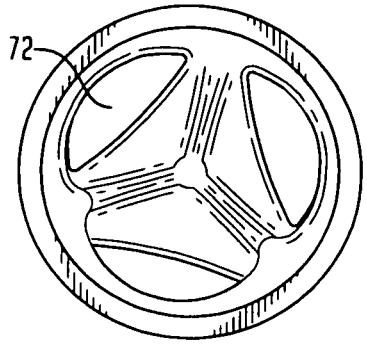
FIG. 7C

VENTRICULAR ASSIST DEVICE FOR INTRAVENTRICULAR PLACEMENT

CROSS-REFERENCE TO RELATED APPLICATIONS

The present application claims benefit of the filing date of U.S. Provisional Patent Applications Nos. 61/198,682, filed Nov. 7, 2008, and 61/065,140, filed Feb. 8, 2008, the disclosure of each of which is hereby incorporated by reference into this application.

BACKGROUND OF THE INVENTION

The present invention relates to intraventricular placement of a ventricular assist device, to components useful in such devices, and to methods of using the same.

In certain disease states, the heart lacks sufficient pumping capacity to meet the needs of the body. This inadequacy can be alleviated by providing a mechanical pumping device referred to as a ventricular assist device ("VAD") to supplement the pumping action of the heart. Considerable effort has been devoted to providing a VAD which can be implanted and which can remain in operation for months or years to keep the patient alive while the heart heals, or which can remain in operation permanently or until a suitable donor heart becomes available if the heart does not heal.

The VAD is typically connected to the heart, most commonly to the left ventricle. For example, a VAD may include a pump which is installed in the body outside of the heart. The VAD may have an inlet cannula connected to the interior of the left ventricle and connected to the intake of the pump. The VAD may also include an outlet tube connected between the outlet of the pump and the aorta. Once connected, the VAD and the heart both pump blood from the left ventricle to the aorta.

As described, for example, in U.S. Pat. Nos. 5,376,114 and 6,217,541 certain VADs having pumps are arranged so that at least a portion of the pump is disposed within the heart when the VAD is implanted within the patient. These VADs incorporate pumps which are connected to separate electric motors by elongated driveshafts. Such shaft-driven pumps suffer from significant drawbacks. Commonly assigned, copending U.S. patent application Ser. No. 12/072,471, the disclosure of which is hereby incorporated by reference herein, discloses a VAD having a unitary pump and motor adapted for positioning within the arterial system as, for example, within the aorta.

Despite the considerable effort devoted to improvements in VADs, still further improvement would be desirable.

SUMMARY OF THE INVENTION

The words "proximal" and "distal" are used herein to denote directions and ends of the device and components. As used herein, when referring the ventricular assist device or components, the term "proximal" refers to the direction toward the surgeon or other operating room personnel during installation of the device and the term "distal" has the opposite meaning.

One aspect of the present invention provides a ventricular assist device for intraventricular placement inside a heart of a mammalian subject. The device preferably includes an anchor element such as a ring configured to be mounted adjacent an apex of the subject's heart, and also desirably includes an elongate member having proximal and distal ends. The device according to this aspect of the invention desirably also includes a pump having a housing, an inlet and an outlet, a rotor within the housing and electric drive coils carried on the housing for magnetically driving the rotor. Preferably, when the device is implanted in the heart, the anchor element and the pump are fixed to the rigid elongate member remote from one another so that the rigid elongate member maintains the pump in position relative to the anchor element and hence with respect to the heart.

In certain embodiments of the device according to this aspect of the invention, the pump may have an axis extending between the inlet and outlet and the rigid elongate member may have an axis offset from an axis of the pump housing. Preferably, the elongate member extends substantially parallel to the axis of the pump.

The elongate member may include a bore extending in the proximal and distal directions thereof, the device further comprising wiring extending through the bore to the pump. The device may further include a tubular outflow cannula defining a bore, the bore having an inlet at a proximal end thereof connected to the outlet of the pump. The outflow cannula preferably includes a tip at the distal end thereof, the tip having at least one opening and desirably having a plurality of openings. Preferably, the tip of the outflow cannula projects through an aortic valve but terminates short of the arch of the aorta.

Another aspect of the present invention provides a ventricular assist device for intraventricular placement inside a heart of a mammalian subject. The device preferably includes an anchor element such as a ring configured to be mounted adjacent an apex of the subject's heart, and also desirably includes an elongate member having proximal and distal ends. The device according to this aspect of the invention desirably also includes a pump having a housing, an outflow cannula preferably having a tip at the distal end thereof. Preferably, the tip of the outflow cannula projects through an aortic valve but terminates short of the arch of the aorta. The ring and the pump are connected to the rigid elongate member remote from another so that the rigid elongate member maintains the pump in position relative to the anchor element.

A further aspect of the present invention provides a method of installing a ventricular assist device in a mammalian subject. The method according to this aspect of the invention desirably comprises mounting a pump to the subject so that an inlet of the pump communicates with the left ventricle of the heart, and positioning an outflow cannula of the pump so that the outflow cannula extends from within the left ventricle through the aortic valve but terminates short of the arch of the aorta.

Yet another aspect of the present invention provides additional methods of placing a ventricular assist device at a location inside a heart of a mammalian subject. The method according to this aspect of the invention desirably comprises providing an anchor element such as a ring and a pump to an elongate member remote from one another so that the elongate member maintains the pump in position relative to the anchor element, advancing the pump through an opening in an apex of the subject's heart and into an intraventricular region of the subject's heart, and mounting the anchor element to an apex of the subject's heart. Preferably, the pump further comprises a tubular outflow cannula, and the pump and cannula are positioned by the anchor element and elongate member so that the tip of the outflow cannula projects through the aortic valve but terminates short of an arch of the aorta.

BRIEF DESCRIPTION OF THE DRAWINGS

FIGS. 7a, 7b and 7c are fragmentary views depicting a portion of a component used in the device of FIG. 1.

DETAILED DESCRIPTION

Figure 1:
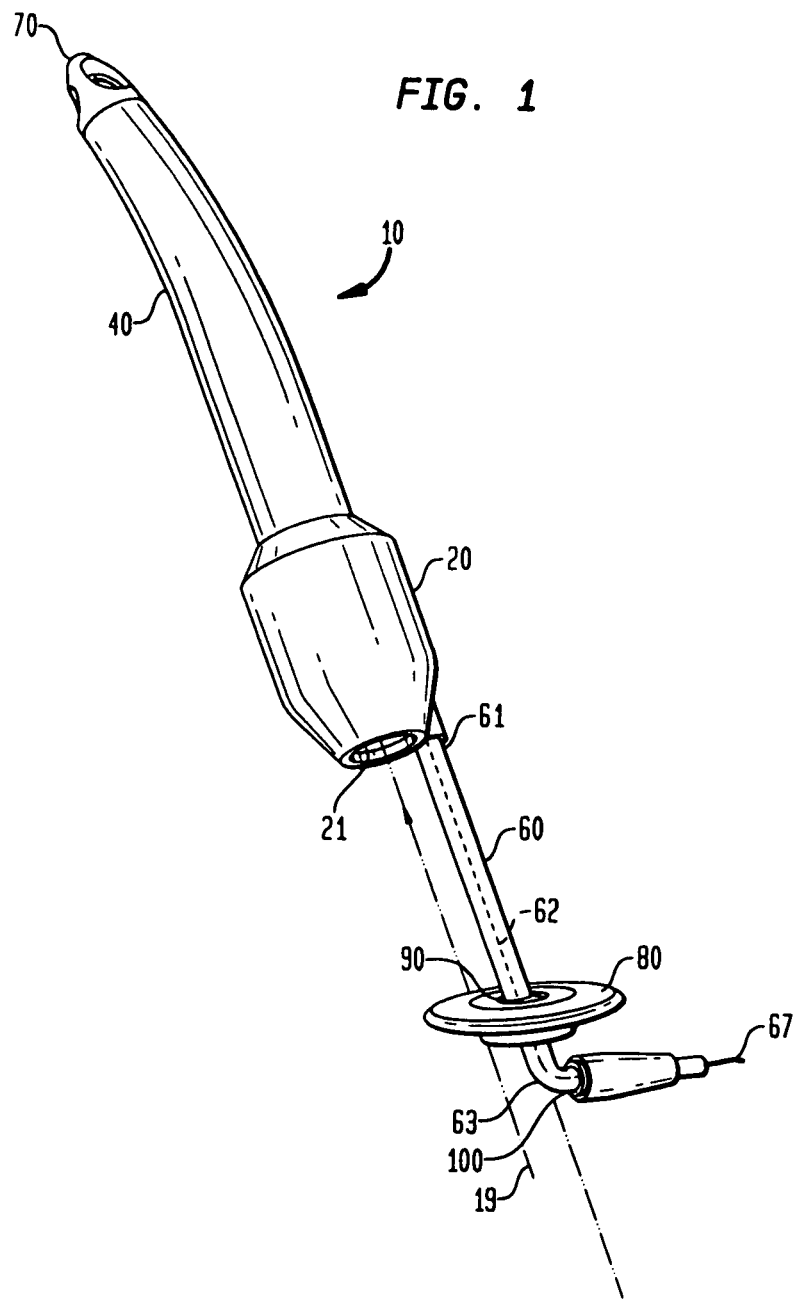
FIG. 1 is a diagrammatic perspective view of a ventricular assist device according to one embodiment of the present invention.
Figure 2:
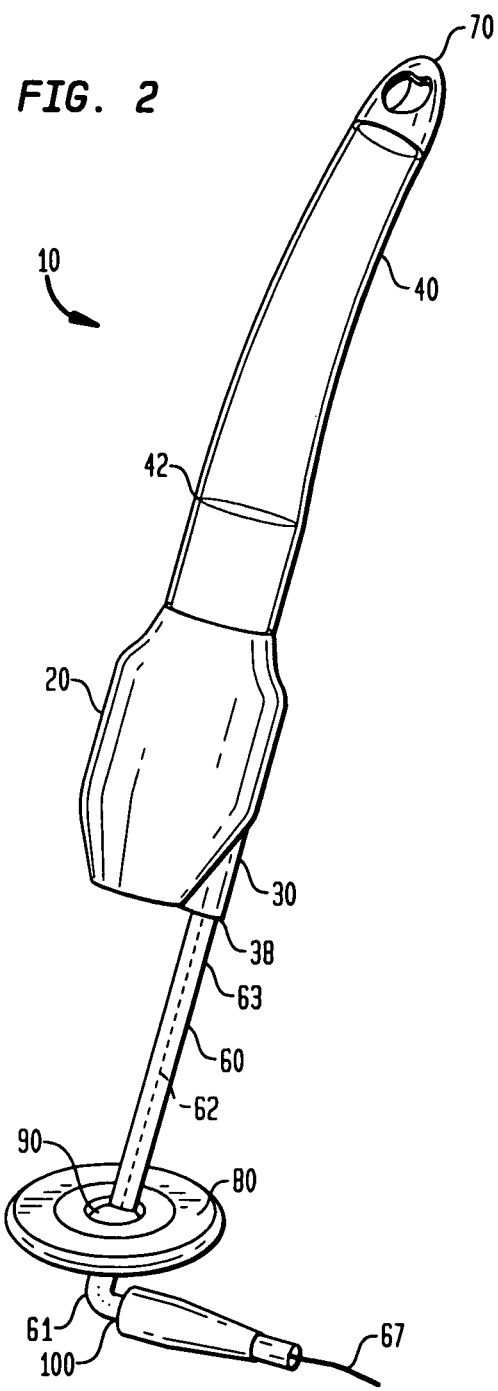
FIG. 2 is diagrammatic perspective view of the device of FIG. 1 from a different perspective.

Referring to the drawings, wherein like reference numerals refer to like elements, there is shown in FIGS. 1-2, an embodiment of the ventricular assist device of the present invention designated generally by reference numeral 10. As shown in those figures, device 10 has four distinct sections including a pump 20, an outflow cannula 40, a rigid elongate member 60, and a ring 80.

Pump 20 is shown in FIGS. 2-5. Pump 20 is an axial flow pump having an inlet 21 and an outlet 23 arranged on an axis 19 referred to herein as the pump axis. The pump has an axial bore 29 defined by a tubular housing 22 which extends between the inlet and the outlet. Housing 22 is formed from biocompatible materials such as ceramics and metals such as titanium. The materials used for those portions of the housing disposed inside the motor stator discussed below desirably are non-magnetic dielectric materials such as ceramics.

A motor stator 24 is disposed around the outside of tubular housing 22. The motor stator is arranged to provide a rotating magnetic field. Preferably, stator 24 contains both magnetic laminations and wire coils (not shown). Sequencing the electrical current through the wire coils produces the rotating electromagnetic field necessary. Stator 24 can be a conventional slotted or slotless design or may utilize a toroidal design.

Figure 6:
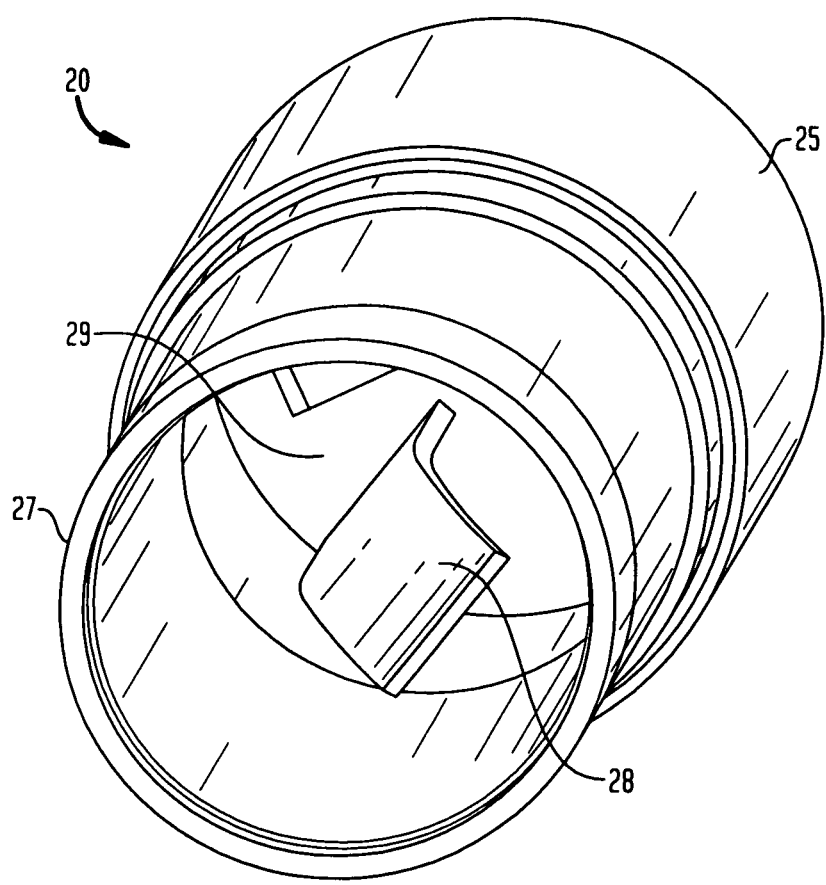

A rotor 26 is disposed within bore 29 shown in FIG. 6, in alignment with stator 24. Rotor 26 may be formed from a unitary piece of a magnetizable, biocompatible platinum-cobalt or platinum-cobalt-boron alloy. The rotor has a central axis coincident with pump axis 19, and includes a plurality of blades 34 projecting outwardly from such axis and curving around the axis in a generally helical pattern having a pitch angle which varies along the axial length of the rotor. The blades define flow channels 36 between them. Blades 34 may be configured so that their circumferential surfaces act as hydrodynamic bearings. Multiple hydrodynamic bearing surfaces may be provided on each blade, spaced along the axial length of the rotor, for greater hydrodynamic stability during operation. These rotor blades 34 may be magnetized for magnetic coupling to motor stator 24. The number of rotor blades 34 is preferably either two or four for symmetry of magnetic poles. During operation, the rotor is driven in rotation at a high rotational speed, typically about 8000 to about 40,000 rpm, and preferably between about 15,000 to about 25,000 rpm. The rotor blades impel blood within the housing axially, toward the outlet 23.

The features of the rotor and stator may be generally as shown in the aforementioned copending, commonly assigned U.S. patent application Ser. No. 12/072,471. However, the pump of this embodiment typically is larger than a pump intended for positioning within an artery. For example, the pump used in this embodiment may be about 21 mm outside diameter and about 34 mm long, and may have a rotor about 10 mm in outside diameter. The pump desirably is arranged to deliver about 4 to 6 L/min flow rate against a pressure head of about 100 mm Hg. As an alternative to the unitary magnetic rotor discussed above, a conventional rotor design involving placement of magnets sealed within a rotor formed from non-magnetic material may be used.

Figure 3:
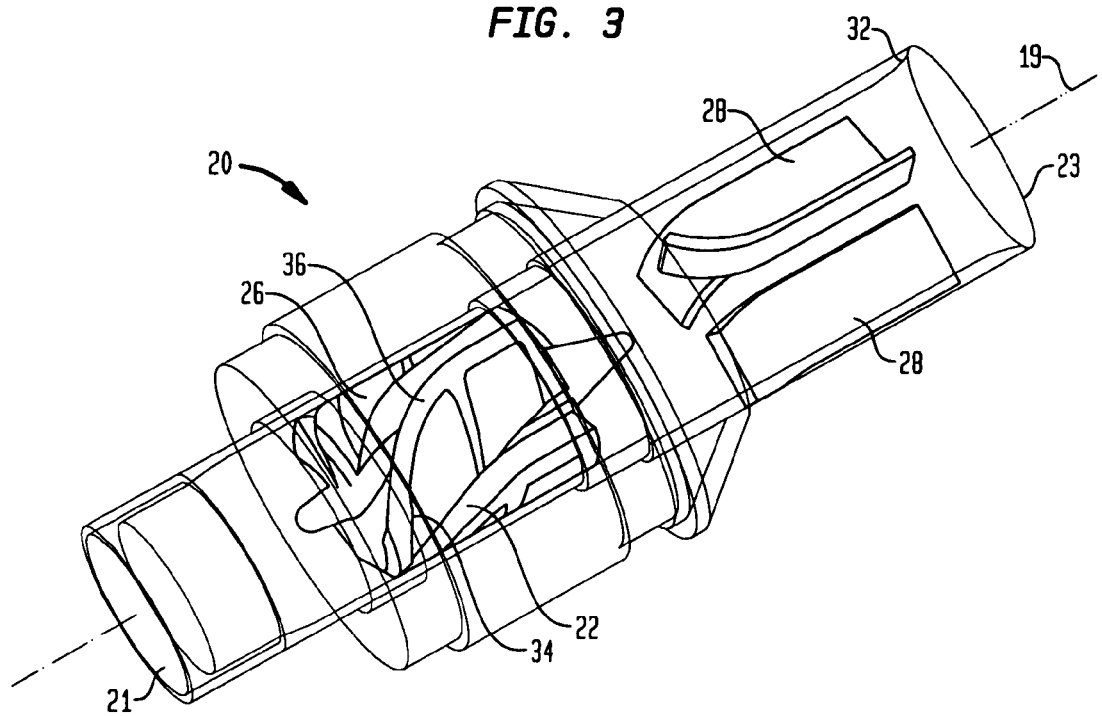
FIGS. 3 and 4 are perspective views of certain components used in the device of FIG. 1.
Figure 4:
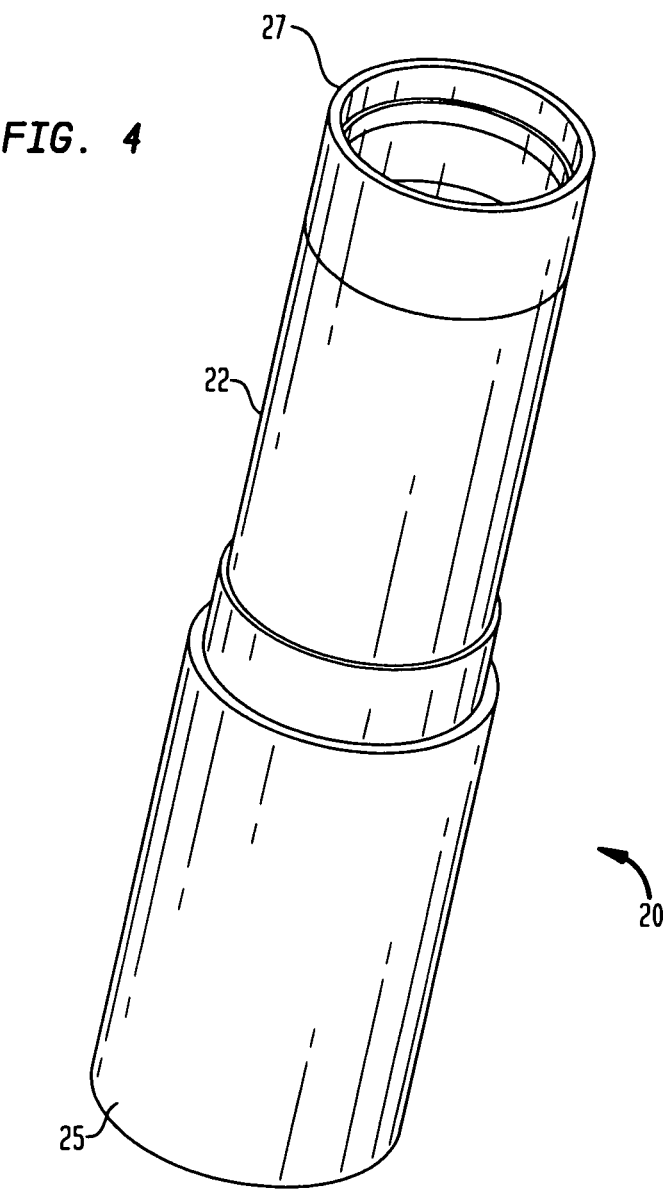
Figure 5:
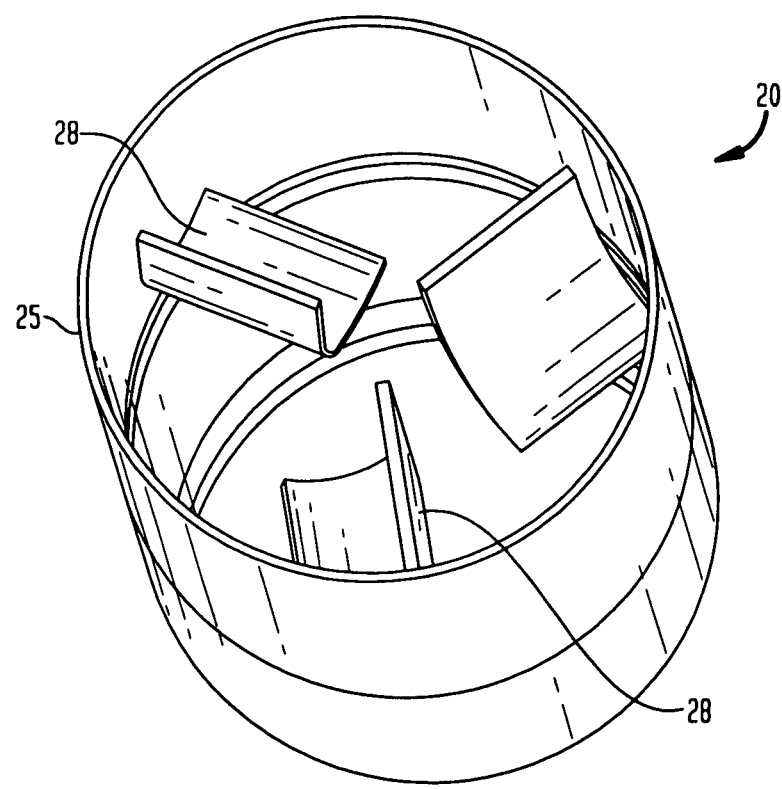
FIGS. 5 and 6 are perspective interior views depicting certain portions of the device shown in FIG. 1.

The pump also includes diffuser blades 28 are mounted within housing 22 downstream from rotor 26, between the rotor and the outlet 23. As best seen in FIGS. 3, 5, and 6, each diffuser blade is generally in the form of a plate-like vane secured to the housing and projecting radially into the bore from the wall of the housing. As best seen in FIG. 3, the upstream ends of the diffuser blades 28, closest to rotor 26, curve in a circumferential direction around the axis 19. The direction of curvature of the diffuser blades is opposite to the direction of curvature of the rotor blades. Preferably, the number of diffuser blades is unequal to the number of rotor blades, and the number of diffuser blades is not an integral multiple or divisor of the number of pump blades. Thus, where the rotor has an even number of blades, the pump desirably has an odd number of diffuser blades, such as three or five diffuser blades 28. This arrangement helps to maximize the stability of the rotor and minimize vibration in operation of the pump. However, it should be understood that two, four, or more than five diffuser blades 28 may be utilized. During operation, the blood passing downstream from the rotor has rotational momentum imparted by the rotor. As the blood encounters the diffuser blades, this rotational momentum is converted to axial momentum and pressure head. Thus, the diffuser blades serve to reclaim the energy used to create the rotational motion and convert that energy to useful pumping work. In this embodiment, the diffuser blades are not attached to one another at the axis. This arrangement conserves space within the bore, and thus maximizes axial flow.

Pump 20 has an exterior shroud surrounding the housing 22 and motor stator 24. The shroud may be formed from a biocompatible metal such as titanium, a ceramic, or a biocompatible polymer. Exterior thromboresistant coatings may also be utilized to improve hemocompatibility. The shroud defines a first attachment portion 30 at the proximal end of the housing, near inlet 21. The first attachment portion 30 (FIG. 2) has a recessed cavity 38 which extends into the shroud in a direction parallel to pump axis 19 but offset from the pump axis.

The apparatus also includes an elongate member 60 which has a proximal end 61, a distal end 63 and a bore 62 therethrough. Preferably, elongate member 60 has an axis along its direction of elongation which axis is parallel to the axis 19 of the pump body but offset from axis 19 in a direction transverse to both axes. Merely by way of example, elongate member 60 may be a tube formed from titanium or other biocompatible metal. Member 60 desirably is substantially rigid. That is, the member desirably is rigid enough to maintain the pump 20 in position, with no substantial movement relative to the ring 80 under the loads normally applied to the system while the system is in place within the heart. Elongate member 60 preferably has a spherical ball 90 mounted along the length thereof, remote from the distal end 63. Ball 90 desirably is fixedly attached to member 60 as, for example, by welding.

The distal end 63 of member 60 is received in recess 38 of first attachment portion 30 of the pump 20. Preferably, the distal end of member 60 is joined to the attachment portion of the pump by a permanent, fluid-tight connection as, for example, by welding member 60 to the pump shroud. Electrical power wiring 67 extends from the stator 24 of the motor through bore 62 of member 60 and out of the member through a fitting 100 at the proximal end of the member. Preferably, there is a fluid-tight feedthrough (not shown) at fitting 100, at the connection between the distal end 63 and the attachment portion of the pump, or both. The electrical wiring extends out of the fitting 100 to a source of electrical power (not shown) external to the body of the patient or implanted within the body of the patient. Preferably, the power source is a transcutaneous energy transfer or "TET" device. Such a device includes an implantable unit which has a battery and an induction coil. The implantable unit typically is mounted remote from the heart, near the patient's skin. Energy is supplied to the induction coil of the implantable unit by an induction coil incorporated in an external unit worn by the patient. The internal battery provides continued operation during intervals when the patient is not wearing the external unit.

An outflow cannula 40 of extends distally from distal end 27 of pump 20. Outflow cannula 40 is generally in the form of a hollow tube having a proximal end attached to pump 20 and communicating with the outlet 23 (FIG. 3) of the pump. The outflow cannula has a tip 70 at its distal end.

Preferably, outflow cannula 40 is a single molded polymer piece made of thermoplastic polyurethanes (segmented and/or copolymerized with silicone, polycarbonate-urethanes, polyether-urethanes, aliphatic polycarbonate, or other additives), silicone, polycarbonate-urethanes, polyether-urethanes, aliphatic polycarbonate, silicone material with or without catalyst metals and possibly sulfonated styrenic polymers. Preferably, outflow cannula 40 may be cast with or without titanium wire structures for bend enhancement properties and non-invasive visualization of a catheter typically under x-ray or fluoroscopy. The outflow cannula 40 may contain barium sulfate or other minerals, or metallic marker bands to provide landmark location visualization by fluoroscopic, CAT or other radiological techniques during or after implantation in the patient.

Outflow cannula 40 may be straight or bent and desirably has an appropriate stiffness and hardness to accommodate the native heart and aortic root geometry and also to have non-traumatic contact with tissues. The diameter of the cannula can be tapered from pump body 20 to a smaller diameter near the distal end of the cannula. As further described below, the distal end of the cannula will project through the aortic valve when the apparatus is implanted in a patient. A cannula which tapers in diameter towards its distal end provides relatively low flow resistance due to its large diameter at the proximal end, but also provides a desirable small diameter portion at the aortic valve. The small-diameter portion at the aortic valve helps to minimize aortic valve insufficiency, i.e. retrograde flow through the valve due to poor sealing of the tri-leaflets around the cannula. Desirably, the cannula is round in cross-section, at least in the region near tip 70 which will extend through the aortic valve when implanted. A round cross-sectional shape also minimizes aortic valve insufficiency. Merely by way of example, a cannula for carrying about 5 l/min of blood may have a mean interior diameter of about 6 mm.

As best seen in FIGS. 7A-7C, tip 70 has a circumferential surface which tapers inwardly toward the axis of the cannula in the distal direction, and thus converges toward the distal extremity 74 of the cannula. In the embodiment illustrated, the distal surface of the tip defines a smooth, dome-like shape at the distal extremity of the tip. A plurality of openings 72 extend through the circumferential surface of the tip. Openings 72 communicate with the interior bore of the cannula. When blood is discharged through openings 72, the flow has a radial component, and will provide a hydrodynamic self centering force for cannula 40. The centering action is believed to further minimize aortic valve insufficiency. Moreover, even if the cannula tip is resting against an arterial wall, the plural openings spaced around the circumference of the tip will still provide good blood flow. The tip 70 geometry is described in more detail in U.S. Provisional Patent Application No. 61/135,004, filed Jul. 16, 2008, and entitled "CANNULA TIP FOR USE WITH A VAD," which application is hereby incorporated by reference in its entirety in the present application.

A family of outflow cannula 40 sizes may be developed to better accommodate the variety of patent native heart sizes. It is preferred that the outflow cannula is preattached to pump 20; however, various cannula sizes may be supplied with the device for attachment in the operating room prior to implantation. The attachment between the outflow cannula and the pump may be of any configuration suitable for maintaining the proximal end in place. The proximal end of the cannula may extend over the distal end of pump housing 22, and may be secured in place by an adhesive bond. Alternatively, a crimp ring may surround the proximal end of the cannula, so that the wall of the cannula is held between the crimp ring and the pump housing.

In this embodiment, the device 10 also includes an anchoring element in the form of a ring 80. Preferably, ring 80 is adapted for mounting adjacent the apex of the patient's heart by sewing around a perimeter of ring 80 to tissue along a wall of the patient's heart. For example, ring 80 may be a metallic structure having a peripheral flange with numerous holes for sewing or stapling the ring to the heart wall. The periphery of ring 80 may be covered with a fabric material such as for example polyester material, expanded polytetrafluoroethylene, felt or the like for promoting tissue growth over the ring to further secure the ring in place. U.S. patent application Ser. No. 11/289,410, entitled "IMPLANT CONNECTOR," teaches such a ring component and is herein incorporated by reference in its entirety in the present application.

Ring 80 preferably includes a spherical socket 84 adapted to engage the spherical ball 90 of elongate member 60 such that ring 80 is pivotally mounted to elongate member 60 remote from pump 20. In the embodiment depicted, the pivotable connection between the ring and the ball may be a permanent connection formed during manufacture. For example, ball 90 may be entrapped between elements of the ring which are permanently connected to one another during manufacture. Ring 80 is configured to align to the heart wall but can also allow for rotational movement to accommodate the native heart movement.

Figure 9:
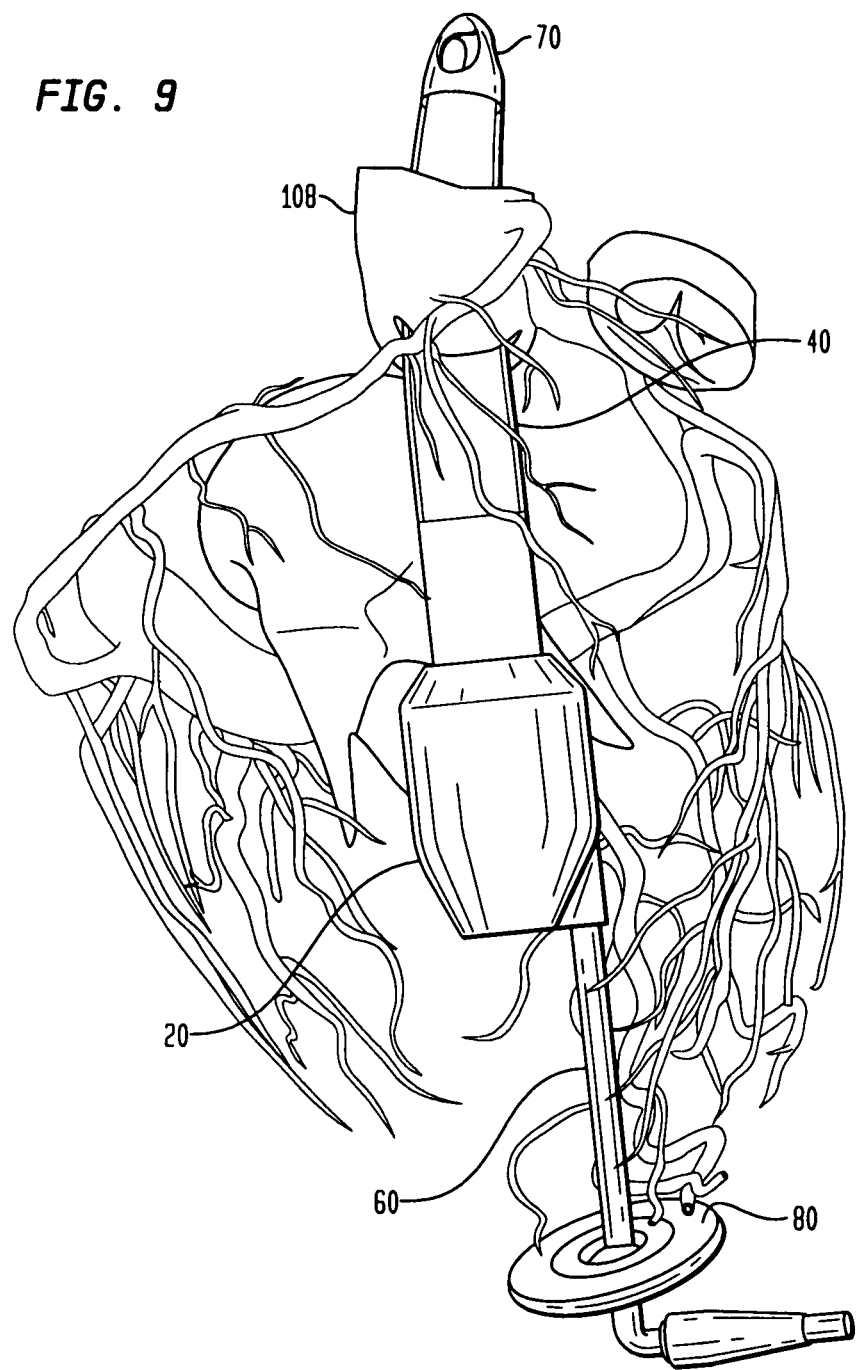
FIGS. 9 and 10 are diagrammatic views of the ventricular assist device of FIG. 1 in an installed condition, in conjunction with the certain structures of the heart.
Figure 10:
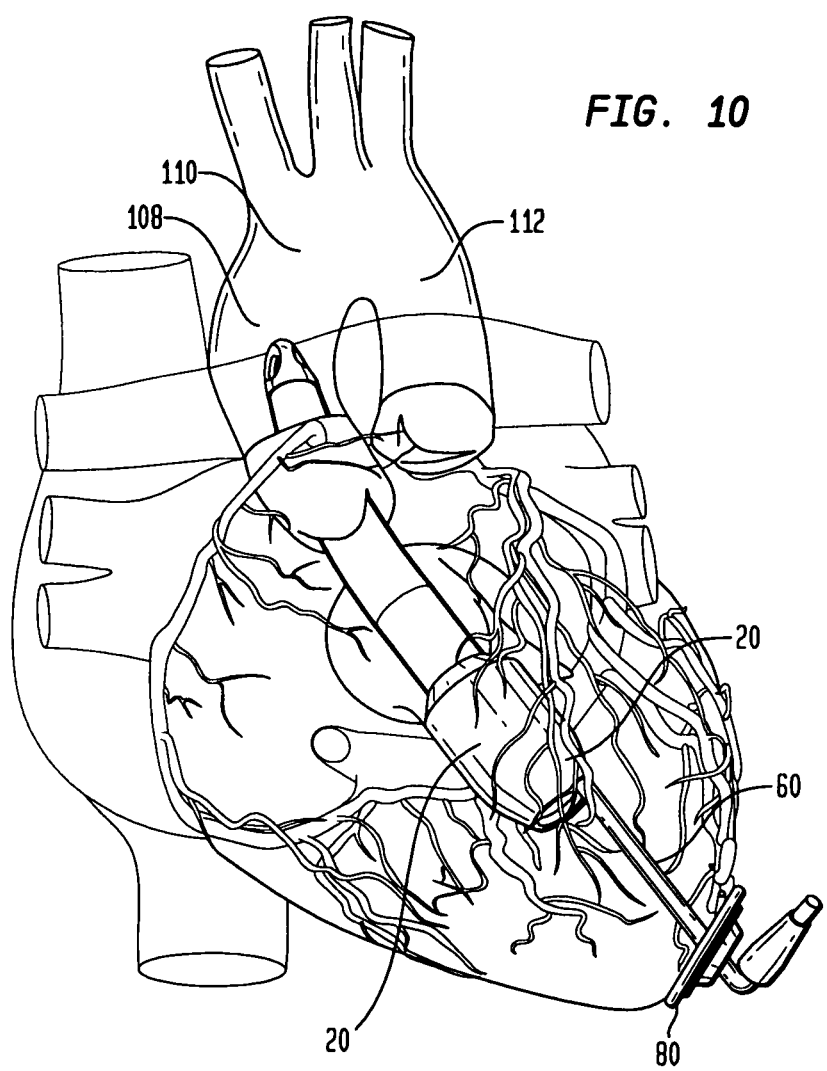

In a method of implantation according to one embodiment of the invention, the apparatus discussed above, including the ring 80, member 60, pump 20 and outflow cannula 40 is provided as a pre-assembled unit. The surgeon gains access to the heart, preferably using a left subcostal or left thoracotomy incision exposing the left ventricular apex. A pledgeted purse string suture is then applied to the epicardium circumferentially over the pump insertion site. A slit incision or an incision in the form of a cross or X, commonly referred to as a "crux" incision, is made through the apex of the heart into the interior of the left ventricle using a cutting instrument such as a scalpel. Pump 20, member 60 and outflow cannula 40 are then inserted through the crux incision or slit incision and positioned within the left ventricle so that cannula 40 extends through the aortic valve into the aorta. Ring 80 is positioned on the outside of the heart as depicted in FIGS. 9 and 10. Proper placement of the components can be verified by fluoroscope or other imaging technique. After placement, the pump can be started by applying electrical power from the external or implantable power source, and proper outflow may be verified using echocardiography. After outflow is verified, crux incision is closed around member 60, as by suturing, and ring 80 is secured to the exterior of the cardiac wall.

As shown in FIGS. 9 and 10, in the implanted condition, ring 80 is mounted adjacent the apex of the subject's heart. Ring 80 and pump body 20 are connected to elongate member 60 remote from one another so that rigid elongate member 60 maintains pump 20 in position relative to ring 80. This maintains the pump and outflow cannula 40 in position relative to the heart.

The aortic valve is one of the valves of the heart. It lies between the left ventricle and the aorta. The ascending aorta 108 (FIG. 10) is a portion of the aorta commencing at the upper part of the base of the left ventricle. The arch of the aorta 110 also known as the transverse aorta begins at the level of the upper border of the second sternocostal articulation of the right side, and runs at first upward, backward, and to the left in front of the trachea. It is then directed backward on the left side of the trachea and finally passes downward on the left side of the body of the fourth thoracic vertebra, at the lower border of which it becomes continuous with the descending aorta 112.

When the device is in the implanted condition shown in FIG. 9, the outflow cannula 40 projects through the aortic valve into the ascending aorta, but most preferably terminates proximal to the arch 110 of the aorta. Thus, tip 70 of cannula 40 is disposed distal to the aortic valve of the subject's heart, but the distal extremity 74 of the tip is proximal to the aortic arch. This position of the outflow cannula 40 is advantageous in that it minimizes contact between the outflow cannula and the walls of the aorta, and thus minimizes trauma and thrombogenesis. The secure positioning of the pump 20 and outflow cannula 40 relative to the heart, provided by ring 80 and member 60, help to allow positioning of the cannula tip just distal to the aortic valve. Because the device is securely held in place within the heart, there is no possibility that movement of the cannula relative to the heart will allow the tip to move proximally, into the ventricle.

In the implanted condition, the axis 19 of the pump extends near the apex of the heart, and the inlet 21 of the pump 20 is aimed generally in the direction toward the apex of the heart. The length of elongate member 60 is such that the inlet 21 of pump 20 is remote from the aortic valve. This position and orientation provide certain advantages. Fibrous structures of the aortic valve, just proximal to the opening of the valve, do not get sucked into the inlet of pump 20. Moreover, the inlet of the pump will not be occluded by the ventricular wall or the interventricular septum of the heart.

The ventricular assist device according to the embodiment discussed above thus provides an intra-ventricular, full output, wearless blood pump that is sized for thoracotomy, subcostal or other implantation method not requiring a sternotomy. The majority of the device sits within the left ventricle and pumps blood distal to the aortic valve to provide cardiac assistance. The patient population which is typically suited for implantation of this device is similar to the bi-ventricular pacing population; congestive heart failure patients who are failing medical therapy and are willing-to undergo a 4 to 6 hour procedure requiring a maximum hospital stay of approximately five days. These patients are very sick and will need 4 to 6 L/min of support initially and may only need 2 to 3 L/min for long term.

Numerous variations and combinations of the features discussed above can be used. For example, device 10 may include dip molded coating of a thin silicone or other polymer around of the exterior of the pump 20, rigid elongate member 60 and ring 80. A dip molded polymer may also be modified by heparin, antithrombotic agents, endothelial tissue growth factors, antibiotics or hydrophilic gels. By extension of the dip molding process as described above the outflow cannula may be formed by the same dip molding process, using a disposable inner core which is removed from the dip-molded cannula before the apparatus is used. Such a process can form the cannula without seams or attachment apparatus as an integral part of the pump housing, and continuous with aforementioned dip coated elements. The anchoring element may be formed or sheathed by dip molded polymer.

In a further variant, the spherical ball 90 used in the arrangement of FIG. 1 is fixed within the spherical socket of the ring or other anchoring element. In yet another variant, the spherical ball and socket may be replaced by a pivotable joint which allows pivoting movement of the anchoring element about just one axis of rotation. In further embodiments, the position of the anchoring element may be adjustable along the length of the elongated element. For example, the anchoring element or ring may include a gripper arranged so that the gripper may be tightened around the elongated member by rotating or otherwise moving one portion of the anchoring element relative to another portion, and so that the gripper may be locked in a tightened condition. For example, the anchor element may incorporate a collet and collet chuck similar to those used to hold machinist's tools. In yet another variant, the elongated member may be threadedly engaged with the anchoring element so that the position of the anchoring element may be adjusted towards and away from the pump by rotating the anchoring element, and then locked in position using a lock nut or other device to prevent further rotation. In still further variants, the elongated member 60 may have appreciable flexibility while still having enough rigidity to maintain the pump and outflow cannula in position. For example, the elongated member 60 may be formed as an elongated coil spring of relatively stiff wire. The electrical wiring extending within the elongated member may be coiled or otherwise convoluted to provide increase resistance to fatigue in flexing.

Figure 8A:
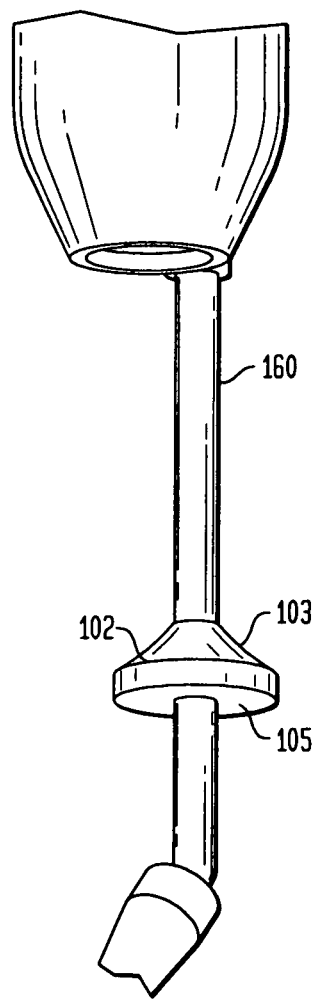
FIGS. 8a and 8b are diagrammatic perspective views depicting portions of devices according to further embodiments of the invention.
Figure 8B:
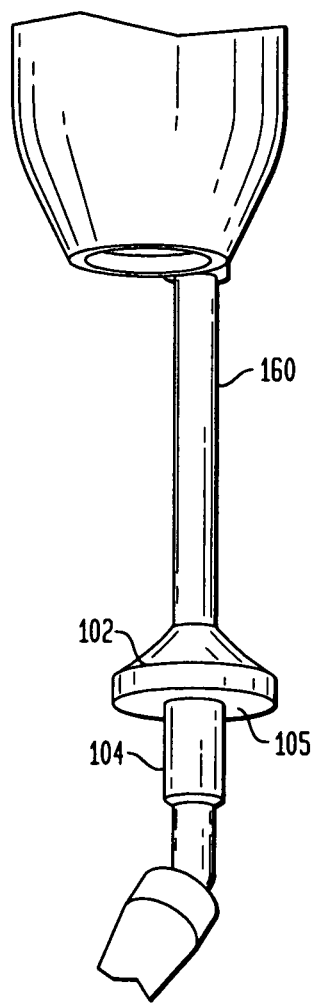

FIGS. 8a and 8b show two alternative configurations of the elongate member and anchoring element. As seen in FIG. 8a, the elongate member 160 has a ring or anchoring element 102 disposed near the proximal end thereof. Anchoring element 102 has a tapered distal surface 103 and a proximal surface 105 which extends substantially perpendicular to the axis of elongation of member 160. In the implantation procedure, anchoring element 102 is advanced into the interior of the ventricle through the crux incision. The incision is closed around the portion of member 160 lying proximal to surface 105, leaving surface 105 of the anchoring element engaged with the interior surface of the myocardium. Purse string sutures may be used on the external myocardium surface Anchoring element 102 acts in a similar manner to the anchoring element or ring 80 discussed above, to prevent axial translation of the elongated member, pump and outflow cannula relative to the heart. When implanted in this manner, the myocardium is closed around that portion of elongate member 160 proximal to anchoring element 102. At this region, rigid member 60 optionally may be provided with a roughened surface, as by sintering, to promote tissue ingrowth for hemostasis. Alternatively, this portion of the elongated member may be left smooth. An interior anchoring element such as member 102 may be used in lieu of, or in addition to, an exterior securement member such as the ring 80 discussed above.

The apparatus shown in FIG. 8b is similar to the apparatus of FIG. 8a, except that the elongated member includes a larger diameter stem section 104 extending proximally from the anchoring element. The enlarged section 104 provides greater surface area for tissue ingrowth. The surface of section 104 may be treated to enhance tissue ingrowth as, for example, by sintering.

In still other configurations, the anchor element may not be a round ring but instead may include one or more feet projecting laterally from the elongated member near the proximal end thereof, the feet being arranged to engage the inside, outside or both of the heart wall adjacent the apex of the heart. Alternatively, the anchor element may be non-circular in cross-section. For example, the anchor element may have other geometric configurations such as triangular, oval, elliptical, or the like.

Figure 11:
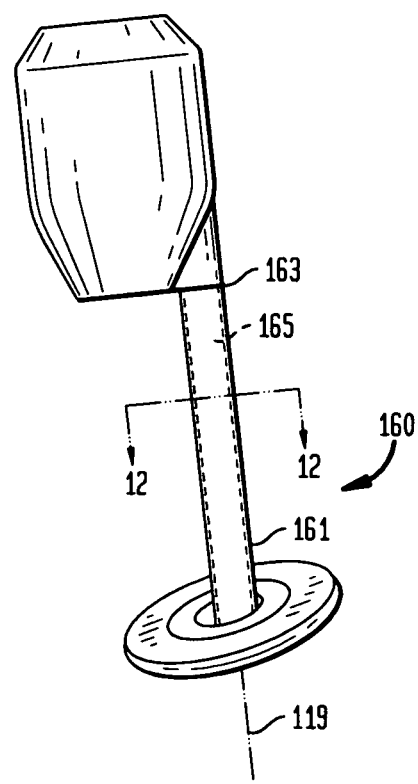
FIG. 11 is a diagrammatic perspective view depicting portions of a device according to a further embodiment.
Figure 12:
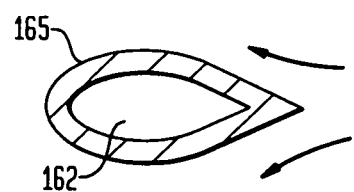
FIG. 12 is a diagrammatic sectional view along line A-A in FIG. 11.

The elongate member may have various configurations. It should be understood that these alternative configurations are merely exemplary and different configurations may be used without departing from the scope of the present invention. As shown in FIGS. 11-12, an elongate member 160 has a proximal end 161, a distal end 163 and a bore 162 therethrough. In this embodiment, elongate member 160 has an axis along its direction of elongation which axis is parallel to the axis 119 of the pump body but offset from axis 119 in a direction transverse to both axes. Elongate member 160 includes a hydrodynamic outer surface 165, i.e. a streamlined surface as seen in cross-section in FIG. 12. The streamlined surface 165 facilitates fluid flow within the left ventricle in the direction across elongate member 160.

Figure 13:
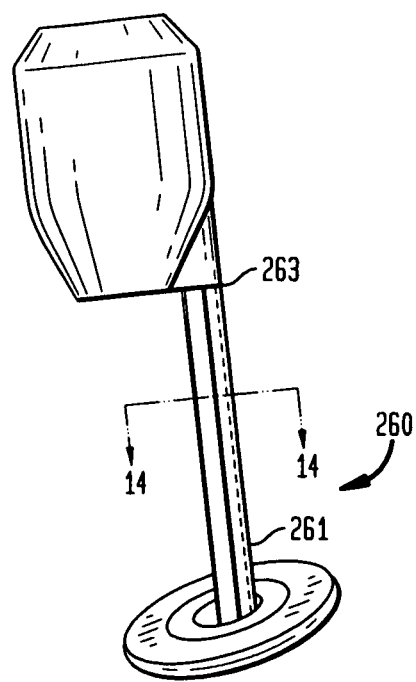
FIGS. 13-19 are diagrammatic perspective views depicting portions of device according to still further embodiments.
Figure 14:
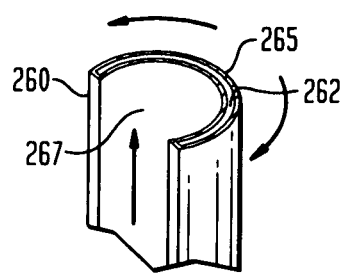

In another variant as shown in FIG. 13, an elongate member 260 has a proximal end 261, a distal end 263 and a bore 262 therethrough. Elongate member 260 is channel shaped and has an outer curved surface 265 and an inner curved surface 267. Distal end 263 is preferably connected to the inlet of the pump. As shown in a perspective view of elongate member 260 in FIG. 14, outer surface 265 is designed to allow blood to easily pass lengthwise along elongate member 260 as designated by the arrow within the channel and into the inlet of the pump. The inside diameter of the channel may be similar to the diameter of the pump inlet. A member of this type may be connected the proximal end of the pump close to the axis of the pump without occluding the flow of blood into the pump. Bore 262 is designed to allow electrical power wiring extending from the stator of the motor to be housed within bore 262.

Figure 15:
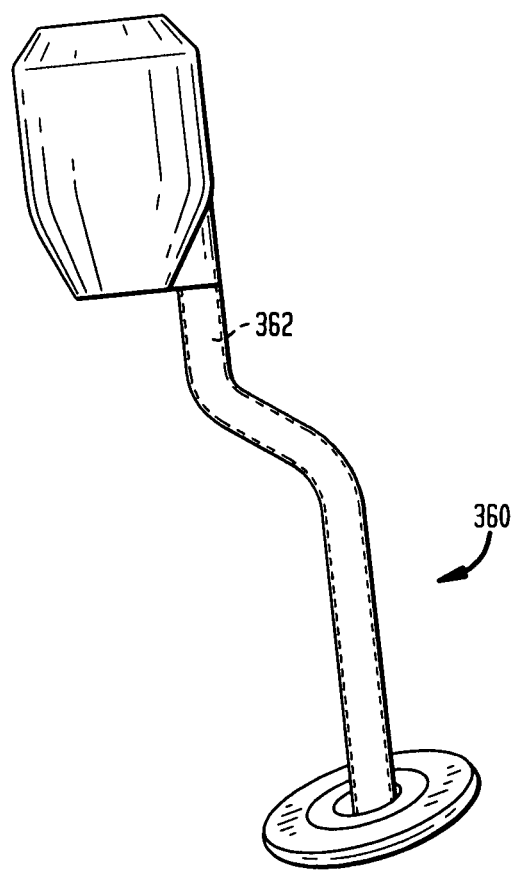

As shown in FIG. 15, an elongate member 360 is curved along the length of the member. Elongate member 360 preferably has a bore 362 structured to allow electrical power wiring to be housed and extend therethrough.

Figure 16:
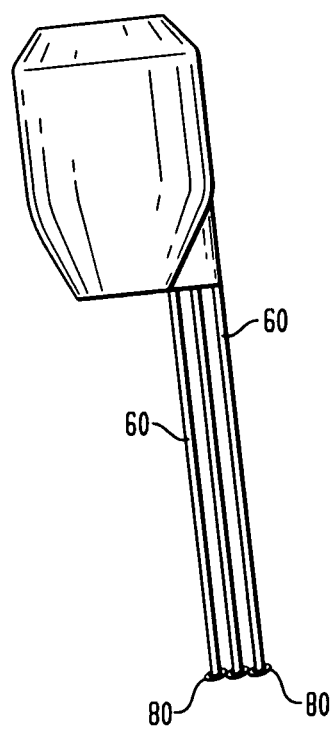

As shown in FIG. 16, the device may include a plurality of anchor elements 80 and elongate members 60. In this embodiment, the plurality of elongate members will preferably have separate attachment points to pump 20. Preferably, the elongate members 60 in this embodiment are substantially parallel to one another. Here again, anchor elements 80 and the pump are fixed to elongate member 60 remote from one another so that the elongate member maintain the pump in position relative to the anchor element.

Outflow cannula 40 may be replaced by a graft lumen material fixed to pump 20 as described herein. The graft lumen may be homologous polyester with gel structure, or impregnated with heparin or thromboresistant materials, or augmented with targeted tissue ingrowth promotion factors such as collagen. Similar to the outflow cannula 40, the graft may be tapered, fitted with a polymer tip, or fashioned into a terminal tip. The tip of the graft may be arranged to provide hydrodynamic self centering as described above.

In a further embodiment, the outflow cannula 40 discussed above with reference to FIG. 1 may be provided with side holes (not shown) extending between the bore of the cannula and an exterior surface of the cannula proximal to the tip 70, in the region of the cannula which will lie within the aortic valve in the implanted condition. Such side holes desirably have greater resistance to flow than the openings 72 of the cannula tip, so that the major portion of the blood flow from the pump will be directed out of the cannula through the tip. However, the blood flow from the side holes tends to reduce impact between the leaves of the valve and the cannula, and to limit damage to the valve. Further, a bolster or cuff (not shown) may be fitted to cannula 40 in a location which will be disposed proximal to the leaves of aortic valve. Such a bolster desirably is arranged to engage the aortic valve root anatomy to maintain a centering force on the cannula and to some degree inhibit retrograde flow. However, such a bolster desirably does not fully occlude forward flow through the aortic valve.

Figure 17:
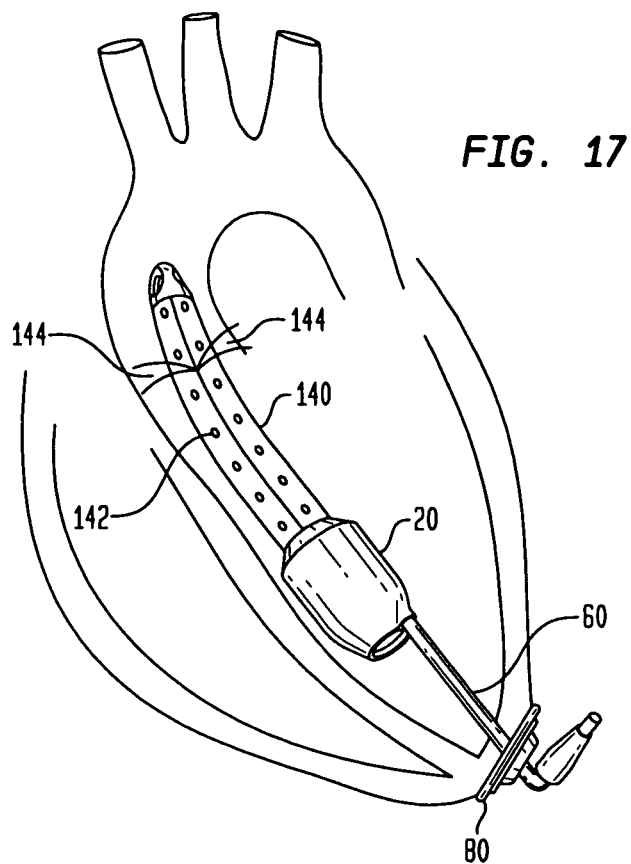
Figure 18:
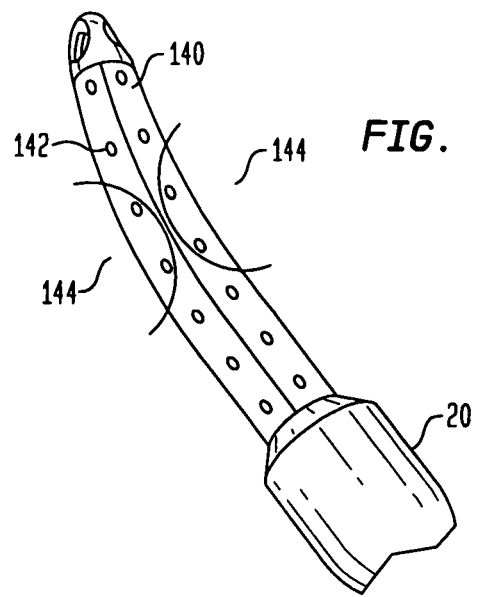

In still other embodiments, the outflow cannula may be non-circular and rather take the shape of other geometric configurations such as triangular, oval, elliptical, or the like. As shown in FIGS. 17-18, outflow cannula 140 is generally triangular in cross-section. Outflow cannula 140 may be straight or bent and desirably has an appropriate stiffness and hardness to accommodate the native heart and aortic root geometry and also to have non-traumatic contact with tissues. Here again, the cross-sectional dimensions of the cannula preferably taper to smaller dimensions in the distal direction, away from pump body 20. Here again, the outflow cannula preferably projects through the aortic valve when the apparatus is implanted in a patient. Here again, the use of a relatively small cross-section at the aortic valve helps to minimize aortic valve insufficiency, i.e. retrograde flow through the valve due to poor sealing of the tri-leaflets around the cannula.

The triangular cross-section of outflow cannula 140 allows each of three separate outer surfaces of cannula 140 to engage a respective leaf 144 of the tri-leaflet aortic valve. The generally triangular cross-section of cannula 140 is configured to allow for superior engagement of an outer surface of cannula 140 with the leaves 144 of the aortic valve. With the generally triangular cross-sectional shape, each leaflet of the aortic valve can engage a side surface of the cannula which is generally flat or which has a large radius of curvature. This enhances the ability of the valve to seal against the cannula. The fixation of anchor element to the apex of the patient's heart also aids in inhibiting pump 20 from rotating about its own axis 19 and therefore helps to maintain the desired orientation of the outflow cannula 140, with each side surface facing a respective leaf of the aortic valve.

Figure 19:
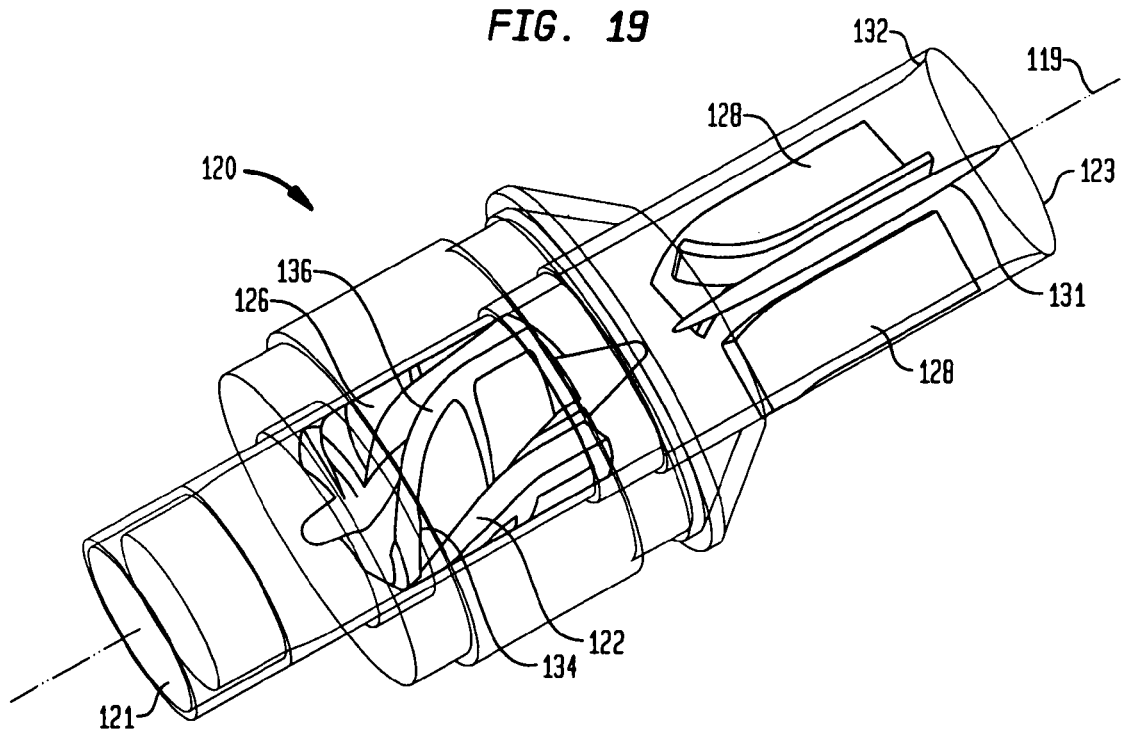

In a further embodiment depicted schematically in FIG. 19, the diffuser blades 128 of the pump, may be connected to a common hub 131 extending along the axis 19 of the pump. The diffuser blades and hub may be fabricated as a separate unit, and this unit may be installed within the tubular housing 122 of the pump distal to the rotor 134.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A ventricular assist device for intraventricular placement inside a heart of a mammalian subject comprising:
   an anchor element configured to be mounted to the subject's heart;
   a rigid elongate member having proximal and distal ends; and a pump comprising a housing, an inlet and an outlet, a rotor within the housing and electric drive coils carried on the housing for magnetically driving the rotor,
   wherein the anchor element and the pump are connected to the elongate member remote from one another,
   wherein the elongate member includes a bore extending in the proximal and distal direction thereof, the device further comprising wiring extending through the bore to the pump, and
   wherein the anchor element includes a spherical socket adapted to engage a spherical ball mounted to the elongate member such that the anchor element is pivotally mounted to the elongate member.

2. The ventricular assist device of claim 1 wherein the anchor element is configured to be mounted to the subject's heart adjacent the apex thereof.

3. The ventricular assist device of claim 1, wherein the pump has an axis extending between the inlet and the outlet, and the elongate member has an axis offset from the axis of the pump.

4. The ventricular assist device of claim 3, wherein the axis of the elongate member is parallel to the axis of the pump.

5. The ventricular assist device of claim 1, wherein the anchor element is fixed to the elongate member.

6. The ventricular assist device of claim 1 wherein the anchor element is a ring adapted for fixation on the exterior surface of the heart wall.

7. The ventricular assist device of claim 1, wherein the elongate member has a hydrodynamic outer surface.

8. The ventricular assist device of claim 1, wherein the elongate member is curved.

9. The ventricular assist device of claim 1, wherein the elongate member is channel shaped.

10. The ventricular assist device of claim 1 having a plurality of anchor elements and elongate members.

11. The ventricular assist device of claim 1, wherein the anchor element is non-circular in cross-section.

12. The ventricular assist device of claim 1 wherein the anchor element is adapted to bear on the interior of surface of the heart wall.

13. The ventricular assist device of claim 1, further comprising a tubular outflow cannula defining a bore, the bore having an inlet at a proximal end thereof connected to the outlet of the pump.

14. The ventricular assist device of claim 13, wherein the outflow cannula includes a tip at the distal end thereof, the tip having a plurality of openings.

15. The ventricular assist device of claim 14, wherein the pump is adapted to be positioned such that the tip of the outflow cannula projects through an aortic valve but terminates short of an arch of the aorta.

16. The ventricular assist device of claim 13, wherein the outflow cannula is tapered in the distal direction.

17. The ventricular assist device of claim 13, wherein the outflow cannula has a generally triangular cross-section at a region proximal to the tip.

18. The ventricular assist device of claim 13, wherein the outflow cannula includes a plurality of side holes extending between the bore of the cannula and an exterior surface of the cannula proximal to the tip of the cannula.

19. The ventricular assist device of claim 1, wherein the anchor element is a ring adapted for mounting adjacent the apex of the patient's heart by sewing the ring to tissue along a wall of the patient's heart.

20. The ventricular assist device of claim 1, wherein the position of the anchor element in the lengthwise direction of the elongate member is adjustable.

* * * * *